United States Patent [19]

Murdock

[11] Patent Number: 4,727,758

[45] Date of Patent: Mar. 1, 1988

[54] FLOW-THROUGH SAMPLING DEVICE

[75] Inventor: David L. Murdock, Lake City, Fla.

[73] Assignee: Occidental Chemical Corporation, Niagara Falls, N.Y.

[21] Appl. No.: 901,219

[22] Filed: Aug. 28, 1986

[51] Int. Cl.$^4$ .............................................. G01N 1/20
[52] U.S. Cl. ............................... 73/863.61; 73/863.24
[58] Field of Search ........... 73/863.61, 863.71, 863.23, 73/863.24, 863.25

[56] References Cited

U.S. PATENT DOCUMENTS

| | | | |
|---|---|---|---|
| 1,837,858 | 12/1931 | Grace | 73/863.71 |
| 2,608,866 | 9/1952 | Breedlove et al. | 73/863.61 |
| 3,582,284 | 6/1971 | Hamshere et al. | 210/791 X |
| 3,712,795 | 1/1973 | Hamshere et al. | 210/791 X |
| 3,966,606 | 6/1976 | Ahmod | 210/136 |
| 4,112,768 | 9/1978 | Holland et al. | 73/863.24 |

FOREIGN PATENT DOCUMENTS 413398  1/1974  U.S.S.R. ........................... 73/863.25

OTHER PUBLICATIONS

"Automated Sampling and Analysis of Wet Process Phosphoric Acid Digestion Systems"; Presented at the Technicon Symposium; Automation in Analylical Chemistry; New York, N.Y., Oct. 2, 1967 by A. N. Baumann et al.; 4 pages.

2 Pages of Incomplete Sampling Related Article with Leading "Feature Report" published by 9-1987.

"Experiences with On-Line Sulfate Analyzer"; Presented at 190th ACS Meeting in Chicago, Ill.; Sep. 9-12, 1985; P. K. Bhattacharjee et al.; 23 pages.

*Primary Examiner*—Tom Noland
*Attorney, Agent, or Firm*—James F. Tao; William G. Gosz

[57] ABSTRACT

A flow-through sampling device is provided for obtaining clear filtrate samples from a pipeline containing a slurry of phosphoric acid and calcium sulphate. The sampling device comprises a sample chamber having inlet and outlet pipes connected to the high pressure and low pressure sides of the pipeline, respectively, the sample chamber having a filter attached to its side portion for removing solids from the slurry prior to obtaining a fluid sample. The sampling device can be equipped with an automatic analyzer for continuously monitoring the composition of the flow stream.

4 Claims, 1 Drawing Figure

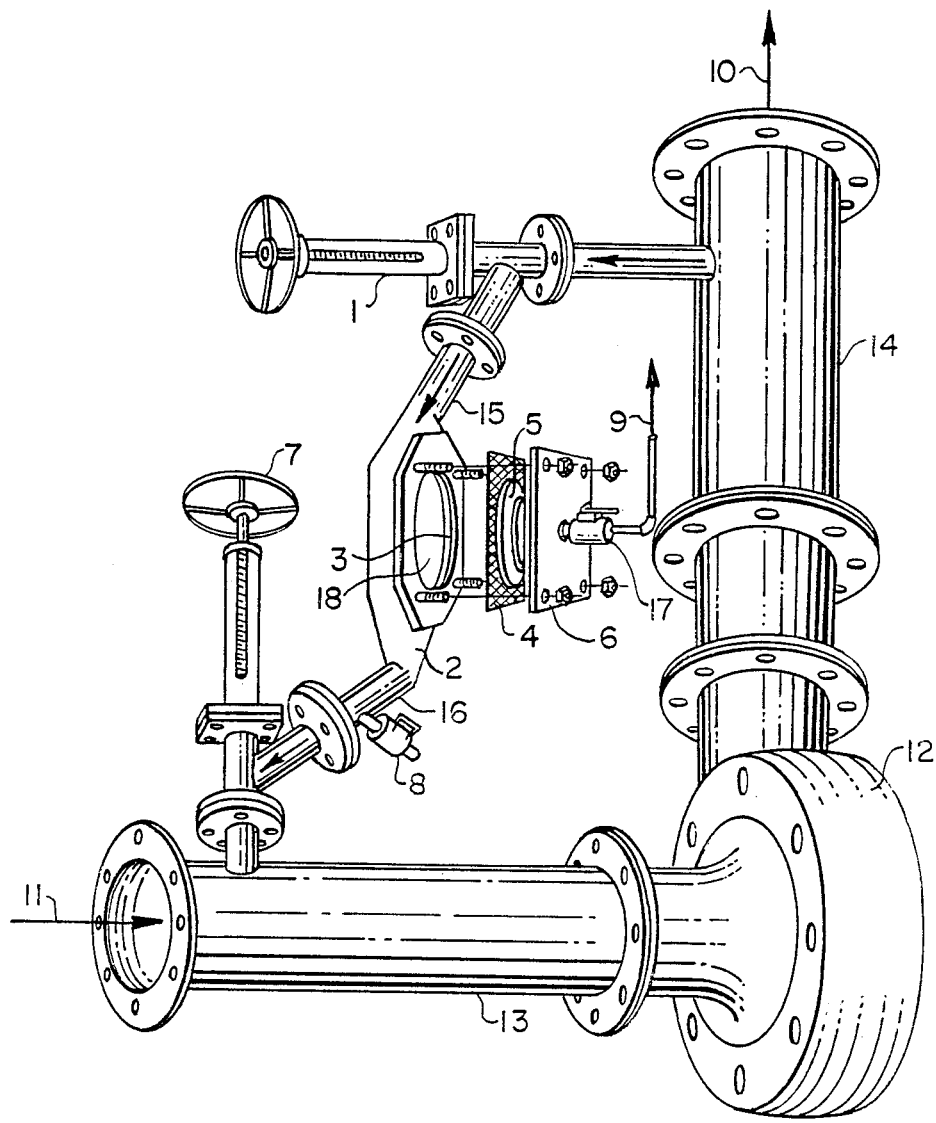

FLOW-THROUGH SAMPLING DEVICE

BACKGROUND OF THE INVENTION

The present invention relates to a flow-through device for obtaining filtrate samples from pipelines which are used to transport slurries, such as fluid slurries in phosphoric acid plants.

The analysis of the composition of fluids at various stages during the production of phosphoric acid in commercial processes is essential for the effective control of product purity and for imporved operating efficiency. Continuous monitoring of product composition is particularly important when a relatively low grade of phosphate rock is available and the conservation of raw materials becomes essential. Various devices for analyzing the composition of process streams and for determining the specific gravity of process fluids, both continuous and manual, have been used in this endeavor.

In particular, accurate sampling of phosphoric acid at various stages of its manufacture is desired for chemical analysis and density determination, such as during the wet process manufacture of phosphoric acid from fluorapatite concentrate. In the wet process, finely ground phosphate rock is dissolved with sulfuric acid in an aqueous medium, precipitating gypsum. The dilute phosphoric acid formed helps to attack the phosphate rock particles, and the solution becomes supersaturated in calcium ions which are then precipitated with the sulfate ions present. The amount of calcium ions in solution is a function of the sulfate concentration, so that control of the sulfate content is necessary to control the crystallization. It is essential to maintain a small excess of sulfuric acid in the digestion slurry to obtain easily filterable and washable gypsum crystals. Separation of the gypsum crystals and the ability to wash them free of the digestion liquors is a determining factor on recovery of feed $P_2O_5$ values in the acid product.

A typical procedure used in the plant for obtaining samples of phosphoric acid involves first purging several gallons of a slurry of phosphoric acid and calcium sulfate through the sample line. A ram valve is used to open and close the sample line. Then, approximately one liter of sample is obtained which is physically carried to a process control lab located nearby. The sample slurry is manually filtered using a laboratory funnel, and the filtrate is then manually analyzed for sulfate content using turbidometric methods.

This procedure is necessarily very cumbersome and time consuming. In addition, a relatively large amount of process slurry must be used to obtain a relatively small quantity of filtrate for analysis. Finally, sampling lines readily become plugged with deposits of solid material thus rendering automated sampling difficult if not impossible. In view of these difficulties, it would be highly advantageous to provide an automated sampling procedure which is relatively efficient in providing quality filtrate samples for analysis.

Various devices and methods have been previously proposed for improving the sampling procedure. It would be desirable to automate the sampling procedure and integrate the sampling apparatus with automatic analyzers.

U.S. Pat. No. 3,582,284 and 3,712,795, both to Hamshere et al., describe an automatic sampling method and device for obtaining samples of sulfate-containing phosphoric acid from plant process vessels such as chemical reactors. U.S. Pat. No. 3,966,606, to Ahmad, also describes a device for obtaining samples of phosphoric acid containing calcium sulfate crystals from process vessels. Additional sampling devices and procedures are discussed by A. N. Bauman and H. H. Roberts in "Automated Sampling and Analysis of Wet Process Phosphoric Acid Systems", *Automation in Analytical Chemistry*, Oct. 2, 1967, and P. K. Bhattacharjee and B. L. Winslow in "Experience with On-Line Sulfate Analyzer", 190th ACS Meeting Sept. 9–12, 1985. However, the disclosed devices require extensive maintenance to prevent component failure and plugging of sampling tubes and lines with precipitated solids. In addition, the pipe that suspends the filter in the reactor must be long enough to reach well below the level of the slurry contained in the vessel. In a large vessel, it is difficult to withdraw the pipe for changing the cloth on the filter or for other service. If the contents of the vessel are maintained at subatmospheric pressure, such as the contents of the crystallizer, it is difficult to service the filter without disrupting the vacuum in the vessel. The pipe is also subject to agitation-induced lateral forces that may damage it or the vessel agitator.

None of the above-identified references disclose flow-through sampling devices which are adapted to obtain clear samples from pressurized pipelines. A flow-through device would have the following significant advantages in comparison to conventional devices: (1) it would provide that the slurry contacting the filter is fresh and representative of slurry within the process, (2) it would provide a means for sweeping away the solids that are periodically backwashed off the sample filter, and (3) it would produce a "scouring" action due to the rapidly moving slurry, thereby preventing the deposition and accumulation of scale on the surfaces of the sampler in contact with the slurry. Sampling from a pressurized pipeline also produces a greater driving force for filtration.

It is therefore a principle objective of the present invention to provide a reliable, flow-through sampling device for obtaining filtrate samples from pressurized pipelines containing a slurry of phosphoric acid and calcium sulfate, which is adaptable for automatic sampling, and which is resistant to failure caused by scaling or plugging due to precipitation formation on the filter surface or in the sampling lines or values.

BRIEF DESCRIPTION OF THE INVENTION

The drawing is a perspective, partially exploded view of the flow-through sampling device of this invention.

SUMMARY OF THE INVENTION

A flow-through sampling device is provided for sampling pipelines containing flowing slurry streams of phosphoric acid and solids such as calcium sulfate. The sampling device comprises an enclosed sample chamber having inlet and outlet means for continuously admitting and withdrawing a fluid slurry, with the inlet means being in fluid communication with the high-pressure side of the pipeline and the outlet means being in fluid communication with the low-pressure side of the pipeline. The sample chamber has an opening in its side portion for diverting a portion of the slurry flowing through the chamber to a filter contained in a filter housing which is sealingly engaged with the opening. Means for regulating the flow of slurry to and from the sample chamber, and for withdrawing a filtrate sample from the filter and for back-washing the filter with water to remove solid deposits are also provided. An automatic analyzer can be connected to the sampling device for automated analysis of sample fluid. The sampling device includes design features which enable the device to be isolated from the sampling system for servicing without disrupting the slurry flow in the pipeline.

DETAILED DESCRIPTION OF THE INVENTION

Referring now to the drawing which illustrates a particular and preferred embodiment of the flow-through sampling device of the present invention, inlet pipe 15 and an outlet pipe 16 are both attached to flow-through sample chamber 2. The inlet pipe, as shown, is connected to and in fluid communication with the high pressure side of pressurized pipeline 14. A slurry of phosphoric acid and solid material, such as calcium sulfate, 10 flows through the pressurized pipeline. The pressure differential is supplied by pump 12. Typical pressure differentials encountered in actual practice are on the order of 25 psig.

A portion of the slurry flows through pipe 15, through sample chamber 2 and exits through outlet line 16 to the low pressure side of pipeline 13 where it joins incoming phosphoric acid stream 11. As depicted in the drawing, the chamber has a tapered configuration with respect to the direction of fluid flow. This feature provides for minimal pressure drop through the sampling device and minimal wear from the abrasive effects of the slurry flowing through the device. The sample chamber also can be configured to have a relatively small internal volume in comparison to the inlet and outlet pipes to minimize slurry retention time (not shown).

The inlet and outlet pipes are equipped with inlet valve 1 and outlet valve 7, respectively. These valves are commercially available and are of the type which can be cleaned, in the case of plugging due to scale formation from the solids contained in the slurry, by moving the ram piston from the open or fully retracted position to the closed or fully extended position and finally back to the open position. This procedure avoids dismantling of the apparatus for routine cleaning. A typical valve is a Strahman 2" ram-type drain valve with a 6" piston extension.

A leaf filter 5 having a filter cloth 4 on its face portion is placed in opening 18 which is disposed in the side portion of the sample chamber. A rubber O-ring 3 which fits between the filter cloth and the sample chamber provides a fluid-tight seal. The filter cloth 4 intercepts solids from the fluid slurry but permits the passage of a clear phosphoric acid filtrate from the sampling device. Preferably, the face of filter leaf 5 is grooved both radially and circumferentially to enhance the flow of filtrate passing through the filter cloth and exiting the sampler through valve 17. This type of filter leaf is commercially available from Albright & Wilson, Limited.

The filter-leaf backup plate or filter housing 6 is provided to secure the filter leaf into position on the sample chamber. The filter housing is mounted to the sample chamber by threaded studs and nuts as shown, which also enable the housing to be rapidly mounted and dismounted for cleaning. Such cleaning may be necessary when, for example, pump 12 is shut down and solids settle out of the slurry, clogging outlet 16. In this event, ram valves 1 and 7 are closed, and the filter leaf assembly is removed by disconnecting the nuts from the threaded studs. Drain valve 8 is opended, and the pluggage is dislodged by directing a stream of water from a hose into opening 18. In practice, this type of non-routine flushing may occur once a week or so.

Valve 17 allows filtrate 9 to exit the sampling device and also permits backwashing of the filter with water after each analytical cycle, e.g. once every 6 or 12 minutes or so. During backwashing, ram valves 1 and 7 remain open, while drain valve 8 remains closed as during normal operation. Water (50 psig) is forced back through the filtrate line in the direction opposite to the direction that the filtrate 9 normally flows. As the backwash water passes in reverse direction through filter cloth 4, the accumulated solids (filter-cake) are dislodged and swept away by the slurry passing through inlet 15 and outlet 16. The cleaned filter cloth is now ready for a new filtration cycle. The backwash water is turned off, and filtrate stream 9 is again allowed to pass out of the sampler to the analyzer for the beginning of a new analytical cycle.

The filtrate sample 9 flows to an analyzer (not shown) for determining the composition of the filtrate. A typical analyzer which is equipped for automatic operation is an an Ionics mode 3000 Digichem analyzer, which is a self-calibrating instrument capable of analyzing either the calcium or sulfate content of phosphoric acid streams.

As depicted in the drawing, the flow-through sampling device is installed in close proximity to the external pump. The inlet valve is installed on the high pressure discharge end of the pump, while the outlet valve is installed on the low pressure suction side of the same pump. In this manner, the sampling device completes a closed fluid circuit through the pump and pipeline. The flow-through sampling device is mounted between the two slurry valves. This configuration ensures a positive pressure driving force through the sample that aids filtration and avoids problems accociated with sampling directly in a large vessel, such as gas seal maintenance, low relative pressures and damaging interactions with the tank agitator.

The sampling device of this invention can be installed anywhere near a pumping station in the slurry line. Typical sampling streams would be the crystallizer slurry at the crystallizer discharge pump, or the dissolver slurry at the dissolver discharge pump. However, the sampling device of this invention can be used to advantage for sampling the contents of any agitated vessel containing a fluid slurry and equipped with a discharge pump by attachment to the pipeline bridging the pump as described herein.

A prototype of the sampling device of the present invention was installed in a commercial wet process phosphoric acid plant at the crystallizer product pump. The inlet and outlet valves were opened and the sampling device was activated. The apparatus produced a clear liquid filtrate, suitable for analysis, with operating cycles consisting of 20 seconds of water back-wash followed by a 6-minute period of acid slurry filtration. A typical filtrate sample size is about two (2) liters total. Only the last 100 cc or so is sent to the analyzer, however.

Although various embodiments of this invention have been shown and described herein, this invention is intended to be liberally construed and not limited by any specific embodiments as will be readily appreciated by those skilled in the art. It is to be understood, therefore, that specific examples are provided by way of illustration only, and that the appended claims are intended to cover all modifications and variations which are within the spirit and scope of the present invention.

What is claimed is:

1. A flow-through apparatus for obtaining fluid samples from a slurry stream of phosphoric acid containing calcium sulfate solids flowing through a pipeline, said pipeline containing a pump for pressurizing the pipeline, said apparatus comprising:

(a) an enclosed sample chamber containing inlet and outlet means for continuously admitting and withdrawing a fluid slurry to and from said sample chamber, said inlet means being in fluid communication with the high pressure side of said pipeline downstream of the pump, and said outlet means being in fluid communication with the low pressure side of said pipeline upstream of the pump, said sample chamber having an opening disposed in a side portion of the chamber for diverting a portion of the slurry flowing through the sample chamber, (b) means for regulating the flow of slurry to and from the sample chamber, (c) a filter housing sealingly engaged with the opening in the side portion of said sample chamber, said filter housing containing a filter which is in fluid communication with the slurry flowing through the sample chamber and being adapted to remove calcium sulfate solids from the slurry stream, and (d) means for withdrawing a filtrate sample from the filter and for backwashing the filter with water to remove solid deposits accumulating on said filter, the flow regulating means permitting the flow of fluid slurry through the apparatus during sample withdrawal and filter backwashing.

2. The apparatus of claim 1 wherein the filter is a leaf-type filter comprising a filter cloth and a filter leaf for mounting the filter cloth.

3. The apparatus of claim 2 wherein the filter housing is a plate which is bolted to the sample chamber.

4. The apparatus of claim 1 wherein the means for regulating the flow of slurry to and from the sample chamber are valves.

* * * * *